US005464413A

United States Patent [19]
Siska, Jr. et al.

[11] Patent Number: 5,464,413
[45] Date of Patent: Nov. 7, 1995

[54] NOSE CLIP

[76] Inventors: William Siska, Jr., 141 Valley View Dr., Elma, N.Y. 14059; Vernon C. Lenz, 3509 Main St., Union Gap, Wash. 98903

[21] Appl. No.: 152,324

[22] Filed: Nov. 15, 1993

[51] Int. Cl.$^6$ ................................................. A61B 17/04
[52] U.S. Cl. ................. 606/151; 606/157; 606/204.45; 606/208
[58] Field of Search ........................ 128/201.18, 206.11; 606/151, 157, 158, 204.45, 208

[56] References Cited

U.S. PATENT DOCUMENTS

| D. 151,651 | 11/1948 | Nield | D32/61 |
|---|---|---|---|
| 246,190 | 10/1977 | Hodge | 606/157 |
| D. 309,809 | 8/1990 | Davidson | D32/61 |
| 598,467 | 2/1898 | Carence | 128/201.18 |
| 640,629 | 1/1900 | Carence | 128/201.18 |
| 2,015,617 | 9/1935 | Claudius | 128/201.18 |
| 2,088,164 | 7/1937 | Dym | 128/201.18 |
| 2,563,236 | 8/1951 | Gragg | 24/518 |
| 2,757,665 | 12/1954 | Tanikawa | 128/201.18 |
| 2,843,115 | 7/1958 | Aufricht | 606/204.45 |
| 3,087,218 | 4/1963 | Fanning, Jr. | D32/61 |
| 4,033,342 | 7/1977 | Lake | 128/201.18 |
| 4,231,360 | 11/1980 | Zloczysti et al. | 128/201.18 |
| 4,445,508 | 5/1984 | Lake | 128/201.18 |
| 4,988,355 | 1/1991 | Leveen et al. | 606/151 |
| 5,011,487 | 4/1991 | Shichman | 606/158 |
| 5,064,429 | 11/1991 | Waterman et al. | 606/151 |
| 5,103,813 | 4/1992 | Hart | 128/201.18 |
| 5,133,724 | 7/1992 | Wilson, Jr. et al. | 606/208 |

FOREIGN PATENT DOCUMENTS

| 299010 | 11/1919 | Germany | 128/201.18 |
|---|---|---|---|
| 427041 | 3/1926 | Germany | 128/201.18 |
| 283716 | 3/1931 | Italy | 128/201.18 |
| 190352 | 12/1922 | United Kingdom | 128/201.18 |

*Primary Examiner*—Aaron J. Lewis
*Attorney, Agent, or Firm*—Freilich Hornbaker Rosen

[57] ABSTRACT

A nose clip is provided, which can be constructed at low cost and which can be smoothly operated to comfortably close noses of different sizes. The clip includes a frame (12, FIG. 1) with a pair of largely vertical bars (14, 16) having nose-squeezing lower ends (20, 22), middles (34, 36) that are pivotally connected, and upper ends (30, 32). A first bar has a pawl (52) on its upper end and the second bar carries a toothed beam (54) that is engaged by the pawl to prevent the upper ends from moving together to thereby keep the lower ends in the nose-squeezing position. The arm middles are connected by an integrally molded flexible and resilient crossbeam (40), and the pawl and toothed beam are integrally molded with the rest of the frame. A person uses the clip by placing pads (24, 26) lying on the lower ends of the bars, against opposite sides of his nose and squeezing the lower ends of the bars until his nose is comfortably closed, at which time one tooth of the multi-toothed beam will engage the pawl.

3 Claims, 1 Drawing Sheet

NOSE CLIP

BACKGROUND OF THE INVENTION:

Nose clips are used to block the nostrils of a wearer when the wearer is breathing through a respirator (when the wearer may be a medical patient or fireman) and for swimmers. Most nose clips are not adjustable, so they may apply more or less than the most comfortable nostril-blocking force. The available nose clips are also somewhat inconvenient to quickly mount on the nose, because they require the person to grasp the nose pads with two hands to pull them apart while placing them on either side of the nose. The prior art shows an adjustable nose clip in U.S. Pat. No. 2,015,617, but this nose clip requires three separately manufactured parts (in addition to the nose pads). Also, it includes latching members with projections that slide over one another, which results in an unreliable and difficult to manipulate latch, and the latch lies under the nose where it may interfere with a respirator. A nose clip which could be constructed at low cost, which operated conveniently and reliably, and which avoided interference with mouth respirators, would be of value.

SUMMARY OF THE INVENTION

In accordance with one embodiment of the present invention, a low cost, reliable, and easily operable nose clip is provided. The clip includes a frame with a pair of largely vertical bars that each have nose-squeezing lower ends and that have higher bar locations that are pivotally connected. A mechanism couples the bars and latches the bars in any one of a plurality of positions to which the lower bar ends have been moved towards each other to progressively squeeze the wearer's nose.

In one nose clip, the high locations where the bars are pivotally connected is at their middles, where a flexible crossbeam integrally molded with the bars pivotally connects them. The latch mechanism includes a pawl at the upper end of one bar and a toothed beam at the upper end of the other bar, with the beam having teeth that progressively move across the pawl as the lower arm ends are squeezed together, and which prevents the upper bar ends from moving closer together to keep the wearer's nose squeezed.

The novel features of the invention are set forth with particularity in the appended claims. The invention will be best understood from the following description when read in conjunction with the accompanying drawings.

DESCRIPTION OF THE PREFERRED EMBODIMENT

Figure 1:
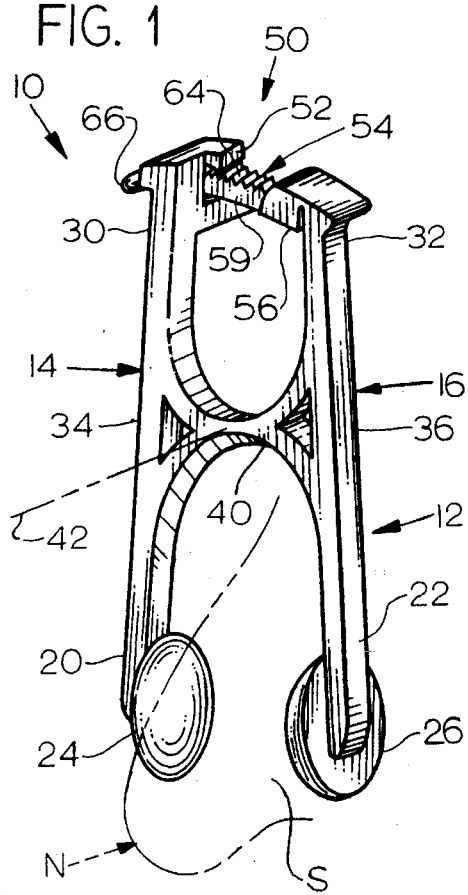
FIG. 1 is an isometric view of a nose clip constructed in accordance with the present invention, shown in its squeezed position.

FIG. 1 illustrates a nose clip 10 which can squeeze the opposite sides S of a person's nose N, at locations immediately above the person's nostrils, to prevent him from breathing through his nose. The nose clip includes a unitary molded frame 12 which has a pair of arms or bars 14, 16 with lower ends 20, 22 that are designed to lie on opposite sides of the wearer's nose. A pair of nose pads 24, 26 are attached to the lower ends of the arms and serve to distribute nose-squeezing pressure.

Each of the bars has an upper end 30, 32 and has a middle 34, 36 lying between the upper and lower ends. A flexible crossbeam 40 connects the middles of the bar to hold them together while allowing the bars to pivot about horizonal axes close to axis 42 so the lower ends of the bars can move together while the upper ends move apart and vice versa.

Figure 5:
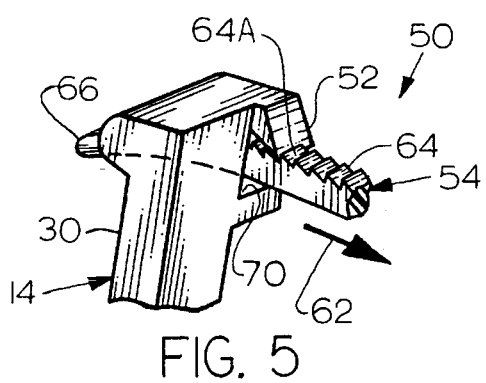
FIG. 5 is an isometric view of a portion of the clip of FIG. 1.

The frame includes a releasable latching mechanism or device 50 that couples the bar upper ends 30, 32. The latching device prevents the upper ends from moving towards each, to thereby prevent the lower ends 20, 22 from moving apart. The latching mechanism includes a pawl 52 formed in the upper end 30 of the first bar, and a toothed beam 54 which has an inner end 56 mounted on the upper end 32 of the second bar. The beam has a base 60 and has teeth 64, with one tooth engaged with the pawl 52. As shown in FIG. 5, the pawl 52 is angled partially in a first direction 62 towards the inner end of the second beam, while a tooth 64A that is engaged with the pawl is angled towards the second bar 14. The engagement of the pawl with a tooth 64A prevents the upper ends of the arms from moving toward each other. As a result, the lower ends of the arms cannot move apart, and they keep the wearer's nose squeezed. The latch device 50 can be released by pressing down an outer end 66 of the toothed beam, to move the beam down in a slot 70 of the first bar and disengage from the pawl. This allows the bar upper ends to move together and the lower ends to move apart.

Figure 2:
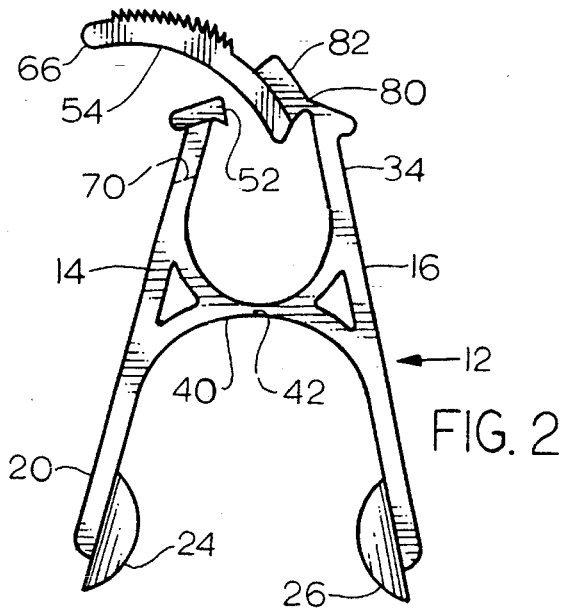
FIG. 2 is a front elevation view of the nose clip of FIG. 1, shown in its originally-molded position.
Figure 3:
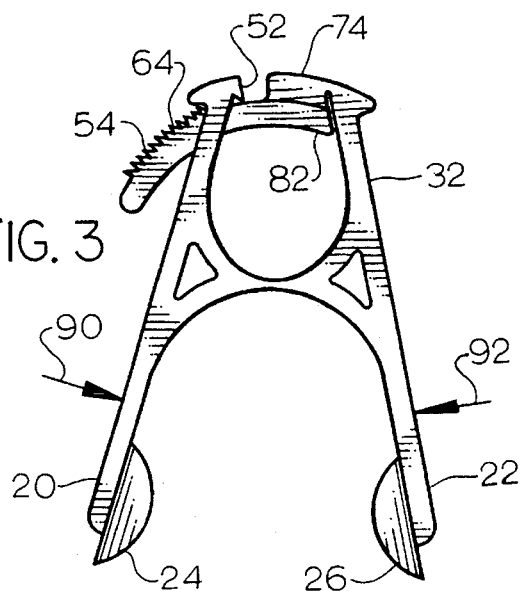
FIG. 3 is a view similar to that of FIG. 2, but showing the clip assembled and in its released position.

FIG. 2 shows the frame 12 in the configuration it assumes when it is molded (but with the pads installed). The beam 12, including the bars 12, 16, the crossbeam 40, the pawl 52, and the toothed beam 54, are all preferably integrally injection molded in a single mold. A variety of engineering plastics can be used, such as a vinyl. The pawl 52 and toothed beam 54 are engaged in use, but are molded in a disengaged position. Applicant forms the frame with a hinge connection 80 which connects the upper end 32 of the second bar to a captured inner end 82 of the toothed beam, the outer end 66 of the beam being free. After the frame is molded, the bar lower ends 20, 22 are squeezed together and the outer end 66 of the toothed beam is inserted through the slot 70 of the first beam. This configuration is shown in FIG. 3, with the beam 74 being pivoted down, and with its inner end 82 abutting the upper end 32 of the second bar. In this configuration, the pawl 52 resiliently deflects the toothed beam 54 slightly downwardly, so its teeth 64 tend to always remain engaged with the pawl.

Figure 4:
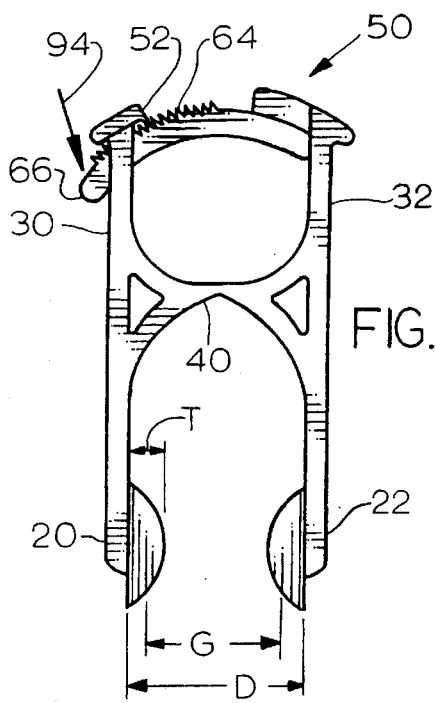
FIG. 4 is a view similar to that of FIG. 3, but showing the clip in its squeezed position.

FIG. 3 shows the nose clip in the released position, wherein the bar lower ends 20, 22 and the corresponding pads 24, 26 are widely spaced. With the clip in this configuration, the lower ends are placed on opposite sides of the wearer's nose and the bar lower ends 20, 22 are pressed together, as indicated by arrows 90, 92, until the wearer senses that his nostrils have been squeezed closed, but the pressure is not so great as to make him uncomfortable. FIG. 4 shows the clip in this configuration, with one of the teeth 64 engaged with the pawl 52. The person releases his fingers from the clip, and the pawl and toothed beam of the latching device 50 keeps the clip in its squeezed position.

The gap G between opposite sides of the person's nose when they are squeezed together to block his nostrils, is about ten millimeters. Of course, the actual distance varies from one person to another. The combined thickness 2T of the uncompressed pads is about 5 mm, or about one-half of the gap G. This thickness is greater than required merely to distribute force against the person's nose for comfort. About half this thickness would suffice for purposes of comfort. Instead, the thickness T of each pad is greater than required for force distribution, so that the pads themselves provide spring resilience. As a result, if there is slight opening of the distance D between the bar lower ends after the person's fingers are removed due to the latching device, this will not significantly decrease the pressure applied to opposite sides of the nose because the resilient pads will maintain a moderate pressure. The pads can be constructed of silicone rubber or resilient foam material.

The clip 10 in its squeezed configuration, can be normally removed from the nose by merely pulling it off, the resilient pads 24, 26 aiding such removal. After the clip is removed, the latching device 50 can be released by the person pushing down against the outer end 66 of the toothed beam, as indicated by arrow 94 in FIG. 4. When the beam outer end is pushed down, the teeth 64 of the beam are released from the pawl 52, thereby allowing the bar upper ends 30, 32 to move together and their lower ends to move apart. The crossbeam 40 is preferably formed of resilient material which tends to spring back to its original position (FIG. 2) so release of the latching device causes the clip to return to its released position of FIG. 3 for reuse. A wearer who is familiar with the release device, can readily release it by pressing down the toothed beam outer end 66 while the clip is on his nose, for a more comfortable removal of the clip.

While the nose clip is shown with the bars extending largely vertically, and with terms such as "upper", and "lower", to aid in the description of the invention, it should be understood that the nose clip can be used in any orientation with respect to gravity. For example, a reclining patient may wear the nose clip, where the bars extend primarily horizontally rather than vertically.

Thus, the invention provides a nose clip which can be easily placed on the nose of a wearer and where the level of nose-squeezing force can be set by the wearer, which operates reliably and can be constructed at low cost. The nose clip includes a frame which includes a pair of largely vertical bars with upper locations, such as their middles, being pivotally connected, and with a latching mechanism that can hold the bars so their lower ends remain together. The latching mechanism is adjustable, to hold the bars together at a plurality of different compression configurations to fit people with different size noses and comfort levels. The bars can have middles that are pivotally connected by a crossbeam and upper ends that are coupled through a latching device that prevents the upper ends from moving towards each other, and all of these parts can be integrally molded.

Although particular embodiments of the invention have been described and illustrated herein, it is recognized that modifications and variations may readily occur to those skilled in the art, and consequently, it is intended that the claims be interpreted to cover such modifications and equivalents.

In the claims:

1. A nose clip comprising:

a frame which includes first and second largely vertical bars, each having nose-squeezing lower ends adapted to press toward opposite sides of a person's nose, upper ends, and a middle, said frame including a bendable crossbeam which connects said bar middles and which can bend to allow said bar lower ends to move together and apart respectively toward a squeezed position and a released position;

said frame including a mechanism that couples said bar upper ends and prevents them from moving toward each other to thereby keep said frame in said squeezed position, said mechanism being releasable to allow said bar upper ends to move toward each other so said frame can move to said released position.

said mechanism comprises a pawl on said first bar upper end and a toothed beam which extends from the second bar upper end to said pawl, with said pawl and toothed beam oriented to prevent said beam upper ends from moving toward each other and with said toothed beam being mutually disengagable from said pawl;

said bars, crossbeam and beam are integrally molded;

said toothed beam has an inner end which forms a molded hinge connection with the upper end of said second bar, to thereby facilitate molding of the beam.

2. A nose clip comprising:

a pair of bars with lower ends designed to lie on opposite sides of a wearer's nose, and with higher bar locations that are pivotally connected;

a latching device that couples said bars and keeps said lower ends progressively closer together as they are squeezed progressively closer together;

said bars each have upper ends and have middles located between the upper and loser ends and forming said higher locations, with said middles pivotally connected, and said latching device includes a pawl formed in the upper end of one bar and a toothed beam extending from the upper end of the other bar and preventing said bar upper ends from moving toward each other.

3. A nose clip comprising:

a frame which includes first and second largely vertical bars, each having nose-squeezing lower ends adapted to press toward opposite sides of a person's nose, upper ends, and a middle, said frame including a bendable crossbeam which connects said bar middles and which can bend to allow said bar lower ends to move together and apart respectively toward a squeezed position and a released position;

said vertical bars and crossbeam being integrally molded of plastic to form a single integrally molded part, said vertical bars being substantially rigid, and said crossbeam being resiliently bendable;

said mechanism comprises a pawl integrally molded as part of said first bar upper end and a toothed beam which is integrally molded as part of the second bar upper end and which extends therefrom to said pawl, with said pawl and toothed beam oriented to prevent said bar upper ends from moving toward each other and with said toothed beam being manually disengageable from said pawl by bending said toothed beam, and with said toothed beam having more teeth than said pawl.

\* \* \* \* \*